(12) United States Patent
Loeffler

(10) Patent No.: US 11,771,589 B2
(45) Date of Patent: Oct. 3, 2023

(54) MOLDED COOLING AND HEATING FACE MASK

(71) Applicant: Joseph Loeffler, Upland, CA (US)

(72) Inventor: Joseph Loeffler, Upland, CA (US)

( * ) Notice: Subject to any disclaimer, the term of this patent is extended or adjusted under 35 U.S.C. 154(b) by 886 days.

(21) Appl. No.: 16/360,440

(22) Filed: Mar. 21, 2019

(65) Prior Publication Data

US 2019/0216638 A1 Jul. 18, 2019

Related U.S. Application Data

(63) Continuation of application No. 15/619,095, filed on Jun. 9, 2017, now Pat. No. 10,314,737.

(51) Int. Cl.
*A61F 7/02* (2006.01)
*B29C 51/30* (2006.01)
(Continued)

(52) U.S. Cl.
CPC ............ *A61F 7/02* (2013.01); *A41D 13/0053* (2013.01); *A41D 13/1107* (2013.01); *A41H 43/04* (2013.01); *B29C 51/30* (2013.01); *B29C 51/421* (2013.01); *A61F 2007/0003* (2013.01); *A61F 2007/0233* (2013.01); *A61F 2007/0295* (2013.01); *B29C 51/08* (2013.01); (Continued)

(58) Field of Classification Search
CPC ................ A61F 7/02; A61F 2007/0003; A61F 2007/0233; A61F 2007/0295; A61F 7/007; A41D 13/1161; A41D 2400/32; A41D 2500/52; A41D 2400/03; A41H 43/04; B29C 51/30; B29C 51/421; B29C 2793/009; B29K 2067/00; B29L 2031/4835; B29L 2031/753; A61M 16/047; A45D 27/003
USPC ........ 607/109; 2/206; 128/858, 863, 201.23, 128/201.24
See application file for complete search history.

(56) References Cited

U.S. PATENT DOCUMENTS 1,715,740 A * 6/1929 Cervelli .................... A61F 7/08
607/109
3,195,539 A 7/1965 Hyman
(Continued)

FOREIGN PATENT DOCUMENTS

CN 201049017 4/2008
CN 205181987 4/2016
(Continued)

OTHER PUBLICATIONS

United States Patent and Trademark Office, Office Action Summary dated Feb. 20, 2018, 14 pages.
(Continued)

*Primary Examiner* — Ophelia A Hawthorne
(74) *Attorney, Agent, or Firm* — Concourse Law Group; Katherine B. Sales, Esq.

(57) ABSTRACT

A molded face mask for treating a user's face, the molded face mask having a rigid, inflexible polycaprolactone body molded to the user's face, the body having: i) two opposed, slightly tapered end portions; ii) a generally straight lower edge; and iii) an upper edge having a concave portion disposed approximately half-way along a length of the upper edge. A kit for providing therapeutic relief and reducing redness and bumps associated with facial shaving.

16 Claims, 7 Drawing Sheets

(51) Int. Cl.
*A41D 13/11* (2006.01)
*A61F 7/00* (2006.01)
*A41H 43/04* (2006.01)
*B29C 51/42* (2006.01)
*A41D 13/005* (2006.01)
*B29K 67/00* (2006.01)
*B29L 31/00* (2006.01)
*B29L 31/48* (2006.01)
*B29C 51/08* (2006.01)

(52) U.S. Cl.
CPC .... *B29C 2793/009* (2013.01); *B29K 2067/00* (2013.01); *B29K 2995/006* (2013.01); *B29L 2031/4835* (2013.01); *B29L 2031/753* (2013.01)

(56) References Cited

U.S. PATENT DOCUMENTS

| | | | | |
|---|---|---|---|---|
| 5,717,993 | A * | 2/1998 | Roberts | A45D 44/12 128/857 |
| 6,098,201 | A | 8/2000 | Boros, Sr. | |
| 6,241,711 | B1 | 6/2001 | Weissberg et al. | |
| 6,397,847 | B1 * | 6/2002 | Scarberry | A61M 16/0605 2/430 |
| 7,559,907 | B2 | 7/2009 | Krempel et al. | |
| 2004/0079374 | A1 * | 4/2004 | Thornton | A61M 16/06 128/200.24 |
| 2012/0318273 | A1 * | 12/2012 | Tsuei | A41D 13/1115 156/204 |
| 2013/0074845 | A1 * | 3/2013 | Smith | A61M 16/0683 128/205.25 |
| 2015/0374945 | A1 * | 12/2015 | Anthony | B29C 51/00 604/179 |
| 2017/0258151 | A1 * | 9/2017 | Roberts | A41D 13/1184 |

FOREIGN PATENT DOCUMENTS

| | | |
|---|---|---|
| CN | 106334269 | 1/2017 |
| DE | 102005042911 | 3/2007 |

OTHER PUBLICATIONS

United States Patent and Trademark Office, Office Action Summary dated Oct. 3, 2017, 8 pages.

* cited by examiner

MOLDED COOLING AND HEATING FACE MASK

CROSS-REFERENCE TO RELATED APPLICATIONS

The present application is a continuation-in-part of United States Non-Provisional Patent Application 15/619,095, now U.S. Pat. No. 10,314,737, titled "Molded Cooling and Heating Face Mask," filed Jun. 9, 2017, the contents of which is incorporated by reference in its entirety.

BACKGROUND

When men shave their faces, the skin can be tender afterwards. This tenderness can lead to an undesirable redness of the skin which can also include undesirable bumps. People's faces also vary greatly with respect to facial features regarding size, arrangement, facial contours, etc. Currently, most people who suffer from bumps and redness utilize aftershave and expensive creams to keep the skin calm. However, placing aftershave and creams on the skin after shaving can also lead to more breakouts, etc. One additional remedy for irritated skin is face masks made from the more well-known gel formulation. The masks typically comprise two layers of some sort of flexible plastic material sealed together around the perimeter, with a gel, or gel beads located between the layers. The problem with this set up is that the gel or gel beads move with gravity, and thus once placed on the face of a user with the user sitting or standing up, the inner contents can shift and pull the mask downward. When a user desires to utilize one of these gel masks, they typically must lie on their back in order to keep the mask in place. This poses a problem when the user has a busy morning/day trying to get ready for work/an evening out.

Consequently, a need still exists for an inexpensive, moldable face-mask that will securely fit the special facial features of the individual wearer so that the user may go about their daily routine while wearing the mask, and at the same time provide therapeutic relief and prevent the undesirable redness and bumps that can be associated with facial shaving.

SUMMARY

The present invention is directed to a moldable face mask that satisfies this need. In a first aspect, the present invention comprises a molded face mask for treating a user's face, the user's face having a nose, the molded face mask comprising: a rigid, inflexible polycaprolactone body molded to the user's face, the body comprising: two opposed, slightly tapered end portions; a generally straight lower edge; and an upper edge having a concave portion disposed approximately half-way along a length of the upper edge; and coupling means for coupling the molded face mask to the user's face.

The face mask can be cooled or heated prior to applying to the user's face.

The coupling means can comprise a first opening disposed proximate the left side edge and a second opening disposed proximate the right side edge.

Optionally, the face mask further comprises one or more straps coupled to the first and second opening for securing the molded face mask to the user's face.

When the mask is worn by a user, the concave portion of the upper edge is disposed below the user's nose.

Optionally, the face mask is placed in a refrigerator for cooling prior to applying to the user's face.

In a second aspect, the present invention is directed to a method of making a molded face mask, the method comprising the steps of: providing a body of polycaprolactone, the body having: two opposed, slightly tapered end portions; a generally straight lower edge; and an upper edge having a concave portion disposed approximately half-way along a length of the upper; placing the body in a heating container; heating the body until it becomes pliable; placing and pressing the pliable body on a face of a user in order to mold to the face of the user; and allowing the pliable body to cool, thereby forming the molded face mask.

Optionally, the method further comprises the step of creating a first opening disposed proximate a left side edge and a second opening disposed proximate a right side edge of the molded mask.

Optionally, the method further comprises the step of coupling one or more straps to the first and second openings for securing the molded face mask to the user's face.

In a third aspect, the present invention is directed to a method of using a molded face mask, the method comprising the steps of: providing the molded face mask; cooling the face mask; and placing the cooled face mask on a user's face after the user shaved their face.

Optionally, the face mask cools to room temperature.

Optionally, the face mask is placed in a refrigerator for cooling.

In a fourth aspect, the present invention is directed to a kit for providing therapeutic relief and reducing redness and bumps associated with facial shaving, the kit comprising a substantially flat sheet of polycaprolactone plastic, the sheet having: two opposed, slightly tapered end portions; a generally straight lower edge; and an upper edge having a concave portion disposed approximately half-way along a length of the upper edge; wherein the sheet can be molded to a user's face to create a rigid case mask.

Optionally, the sheet has a length of from about 10.5 inches to about 12.5 inches, a height of from about 4.5 inches to about 6.5 inches, and a width of from about ⅛ inch to about 3/16 inch.

Optionally, the kit can further comprise one or more straps for coupling the mask to the user's face.

DRAWINGS

These and other features, aspects, and advantages of the present invention will become better understood with reference to the following description, appended claims, and accompanying drawings where:

DESCRIPTION

As used herein, the following terms and variations thereof have the meanings given below, unless a different meaning is clearly intended by the contest in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers ingredients or steps.

Figure 1:
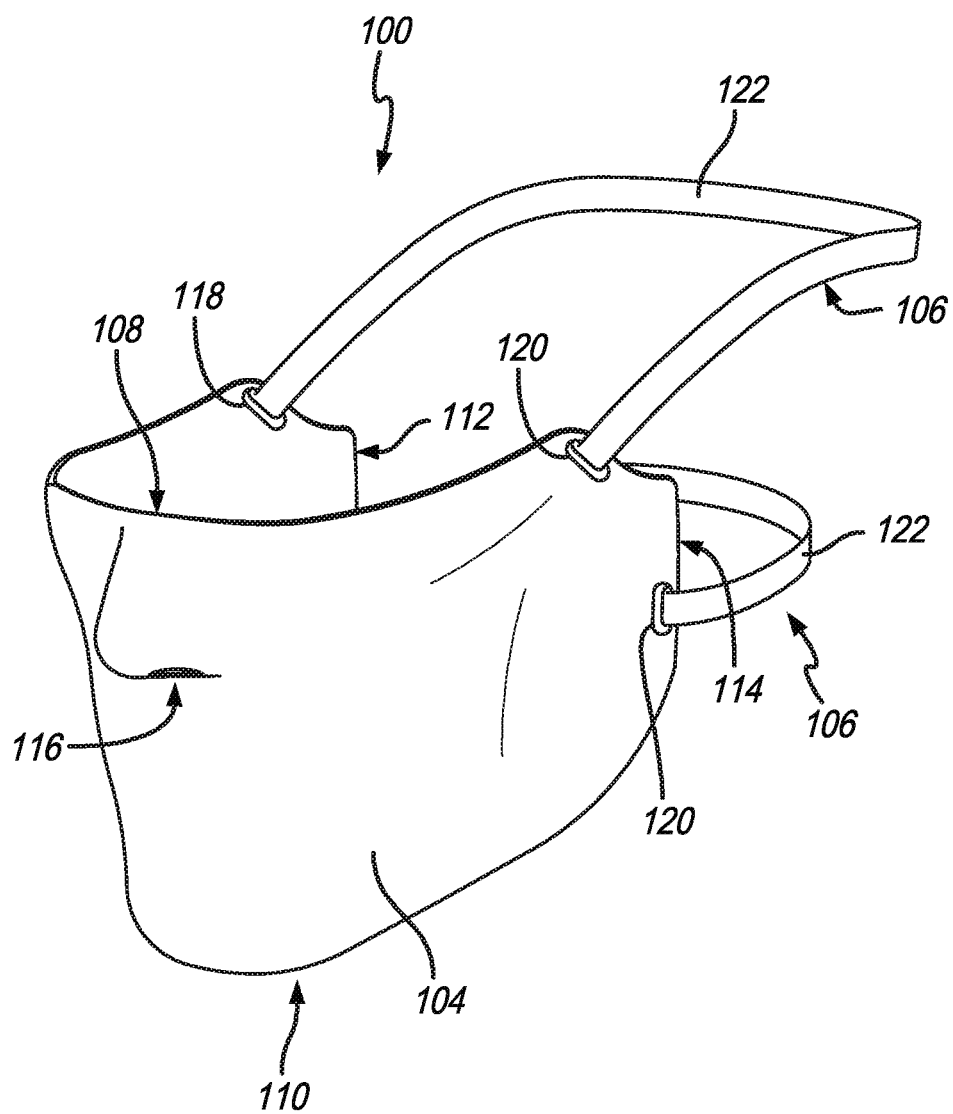
FIG. 1 is a perspective view of a moldable face mask having features of the present invention.
Figure 2:
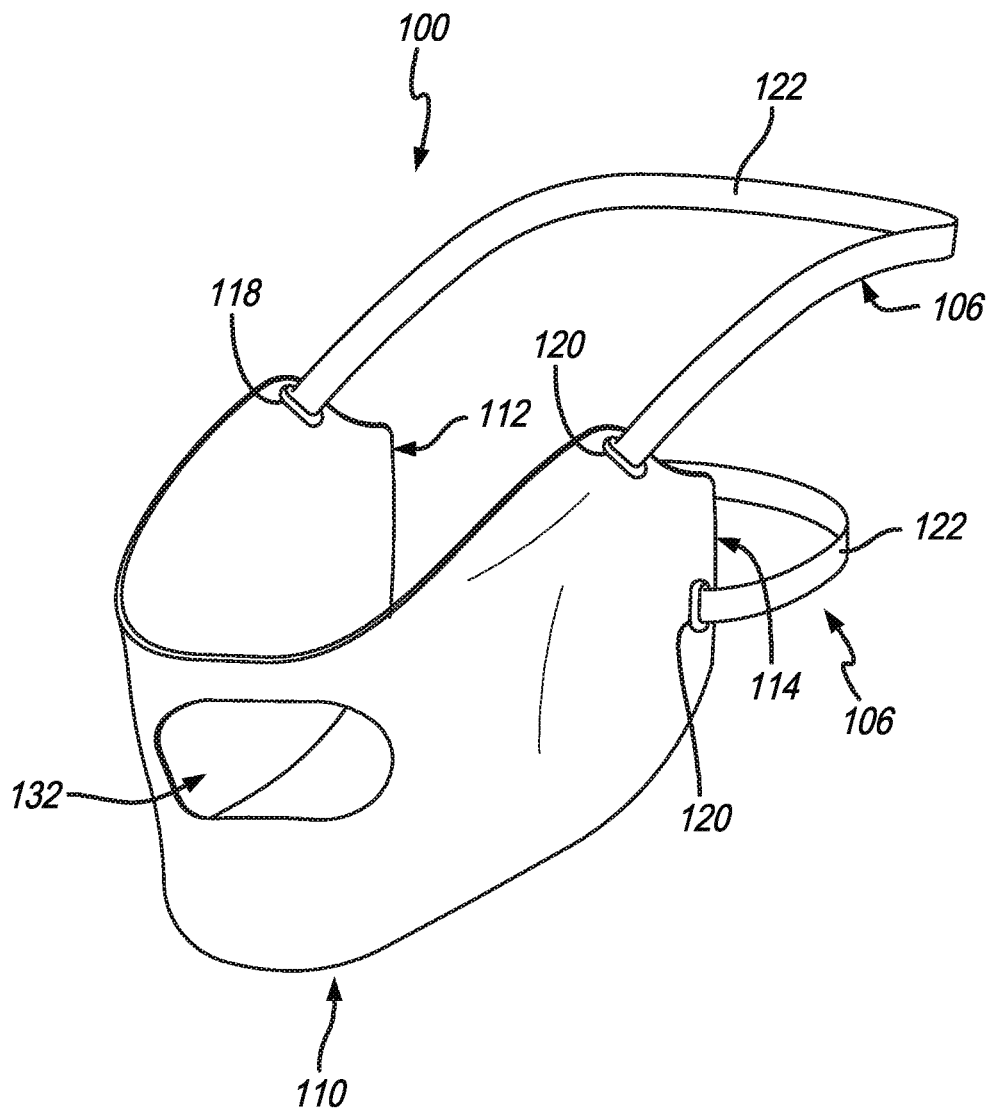
FIG. 2 is a perspective view of a moldable face mask having features of the present invention, wherein the mask does not cover the user's nose.
Figure 3:
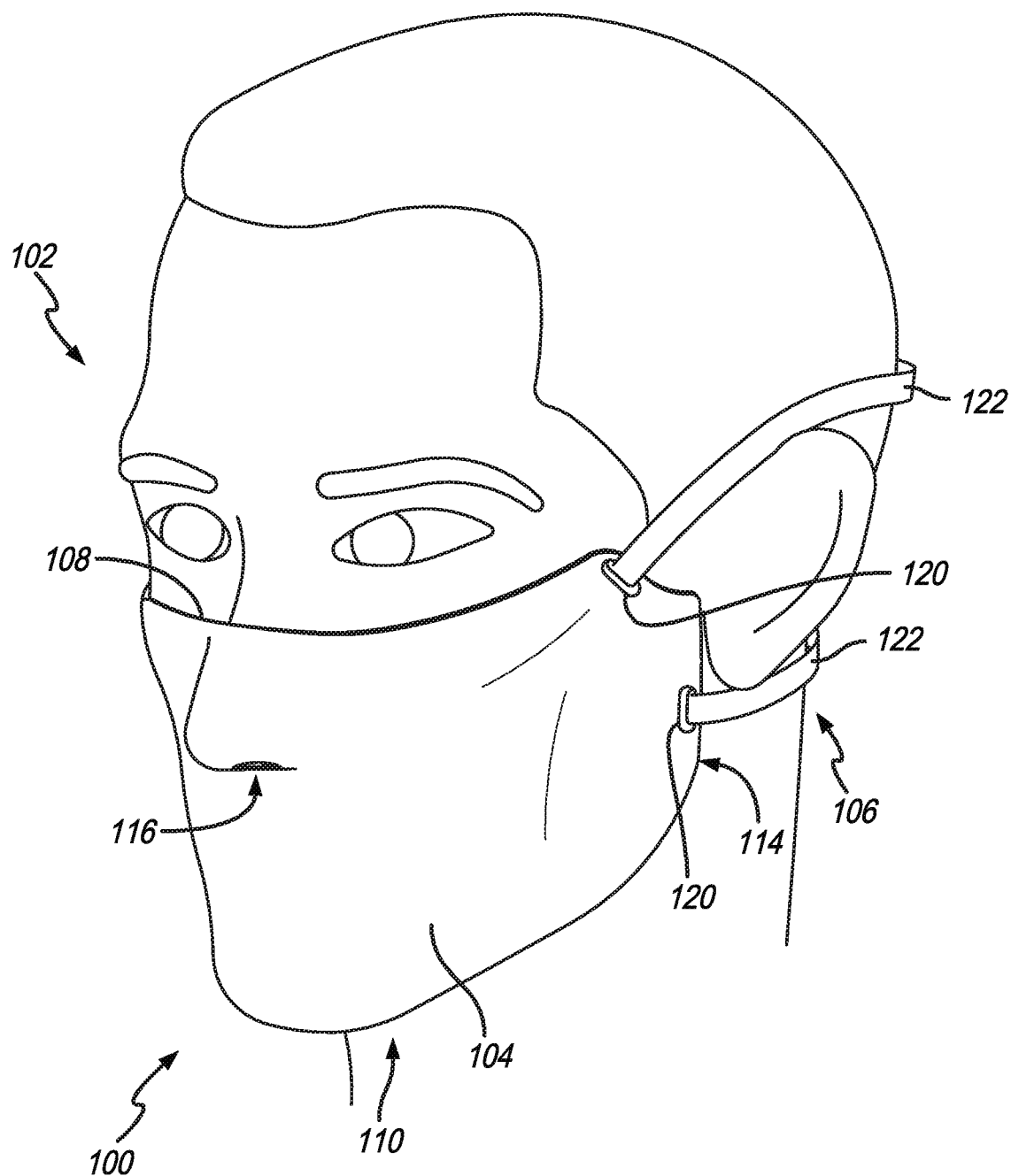
FIG. 3 is a perspective view of a user wearing the face mask shown in FIG. 1.

Referring now to FIGS. 1-3, there is shown a moldable face mask 100 for treating a user's face 102, the moldable face mask 100 comprising a rigid, inflexible body 104 molded to the user's face 102 and a coupling means 106 for coupling the molded face mask 100 to the user's face 102. The body 104 comprises a top edge 108, a bottom edge 110, a left side edge 112 and a right side edge 114. The body 104 can be made from any kind of plastic or resin material that is bio-compatible (i.e. not harmful to living tissue) and can endure heating and cooling without affecting the shape of the molded mask 100.

Preferably the body 102 is made from polycaprolactone (PCL). PCL is a biodegradable polyester with a low melting point of around 60° C. and a glass transition temperature (i.e. the temperature region where the polymer transitions from a hard, glassy material to a soft, rubbery material) of about −60° C. The most common use of PCL is in the manufacture of specialty polyurethanes. PCL imparts good water, oil, solvent and chlorine resistance to the polyurethane produced. PCL is degraded by hydrolysis of its ester linkages in physiological conditions (such as in the human body) and has therefore received a great deal of attention for use as an implantable biomaterial. In particular it is especially interesting for the preparation of long term implantable devices, owing to its degradation which is even slower than that of polylactide.

In a typical embodiment, the top edge 108 is disposed proximate the user's nose, and can either lie above (as shown in FIG. 1) or below (as shown in FIG. 2) the user's nose. Placement depends entirely on the preference of the user. Similarly, the bottom edge 110 is disposed proximate the user's chin, and in most cases will lie below the users chin in order to provide adequate coverage of the skin on the chin and neck that was shaved. Optionally, if the user desires greater coverage, the bottom edge 110 can lie further down the user's neck, to provide adequate cooling to the shaved neck skin. However, it should be noted that the location and position of the top and bottom edges 108, 110 is entirely up the user, as the mask 100 is made by the user to their desired specifications.

The body 104 can optionally comprise at least one nostril opening 116 disposed proximate a user's nostril. Additionally, the body 104 can comprise at least one mouth opening 132 disposed proximate the user's mouth.

In one embodiment, the coupling means 106 comprises at least one opening 118 disposed proximate the left side edge 112 and at least one opening 120 disposed proximate the right side edge 114. Optionally, as shown in FIGS. 1-3, the coupling means comprises two openings 118 disposed proximate the left side edge 112 and two openings 120 disposed proximate the right side edge 114.

One or more straps 122, which can comprise elastic cords or any other material that can be used to affix the mask 100 to the wearer's face, are either permanently or detachably secured to the one or more openings 118, 120, In this manner the mask 100 can be mounted to the head 102 of a wearer with the straps 122 passing behind the head and generating sufficient tension due to stretching to hold the mask 100 in place without riding up or down on the wearer's face. The straps 122 can be any feasible diameter, but it is anticipated the most typical application will be between about ⅛ to ½ inch in diameter.

Optionally, the coupling 106 means comprises a hook and loop coupling system for securing the one or more straps 122 to the face mask 100.

Figure 4:
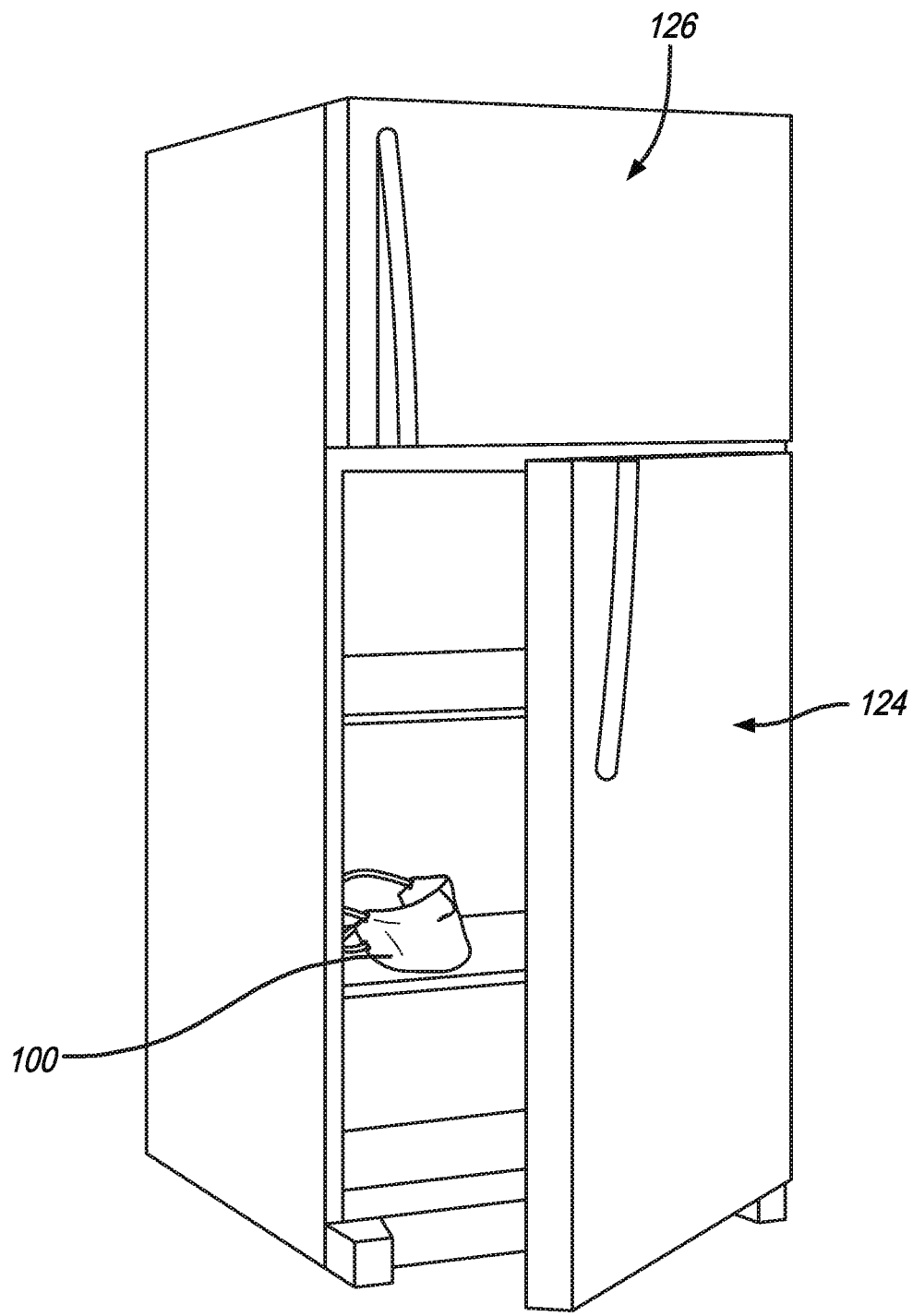
FIG. 4 is a perspective view of the face mask of FIG. 1, wherein the face mask has been placed in a refrigerator for cooling.

Referring now to FIG. 4, the mask 100 is used in the following manner. First, a user places the mask 100 in a cooling location. The cooling location can either in a room at room temperature, or in a refrigerator 124 or freezer 126, as illustrated in FIG. 4. Once the mask 100 has cooled to the desired temperature, the user then places the cooled mask 100 on their face 102, and secures the mask 100 to their face 102 using straps 122. Optionally, the mask 100 can be heated rather than cooled, if heat therapy is desired. The mask 100 could be placed in a microwave, in an oven, or in hot water in order to impart the desired heat to the mask 100.

Because the mask 100 is comfortably secured to the users' face 102, the user can continue about their morning routine such as getting ready for work. This is also made possible because of the rigid plastic the mask 100 is made from. If the mask 100 comprised the more well-known gel formulation, the mask 100 would be unduly heavy, and sag, pulling on the face 102 of the user. In stark contrast, the mask 100 of the present invention is lightweight, and because it does not comprise any sort of gel or moveable filling material, there is no shift in weight downward.

Figure 5:
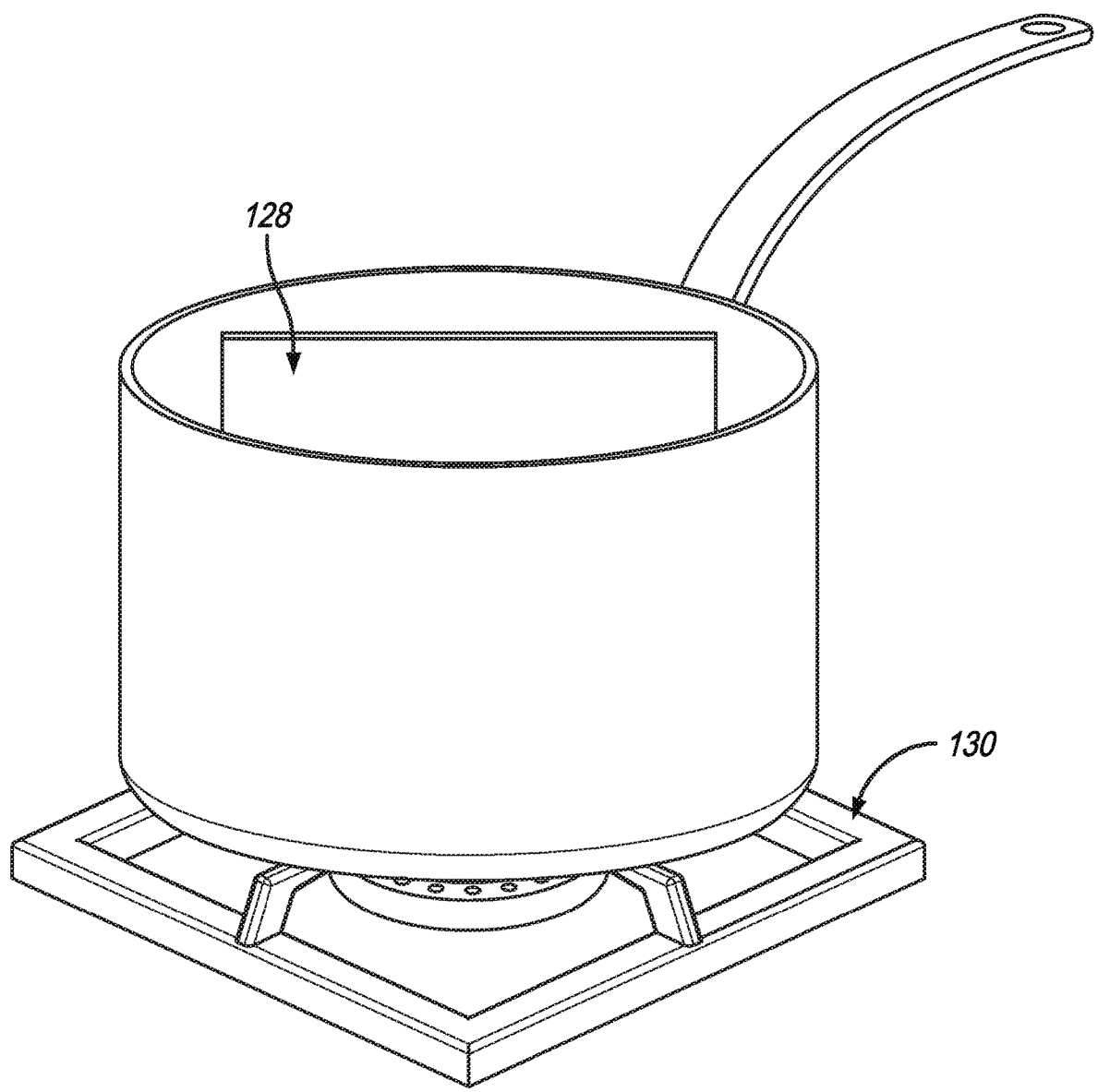
FIG. 5 is a perspective view of a method of making the face mask of FIG. 1, wherein a sheet of plastic has been placed in a pot on a stove for heating and melting.
Figure 6:
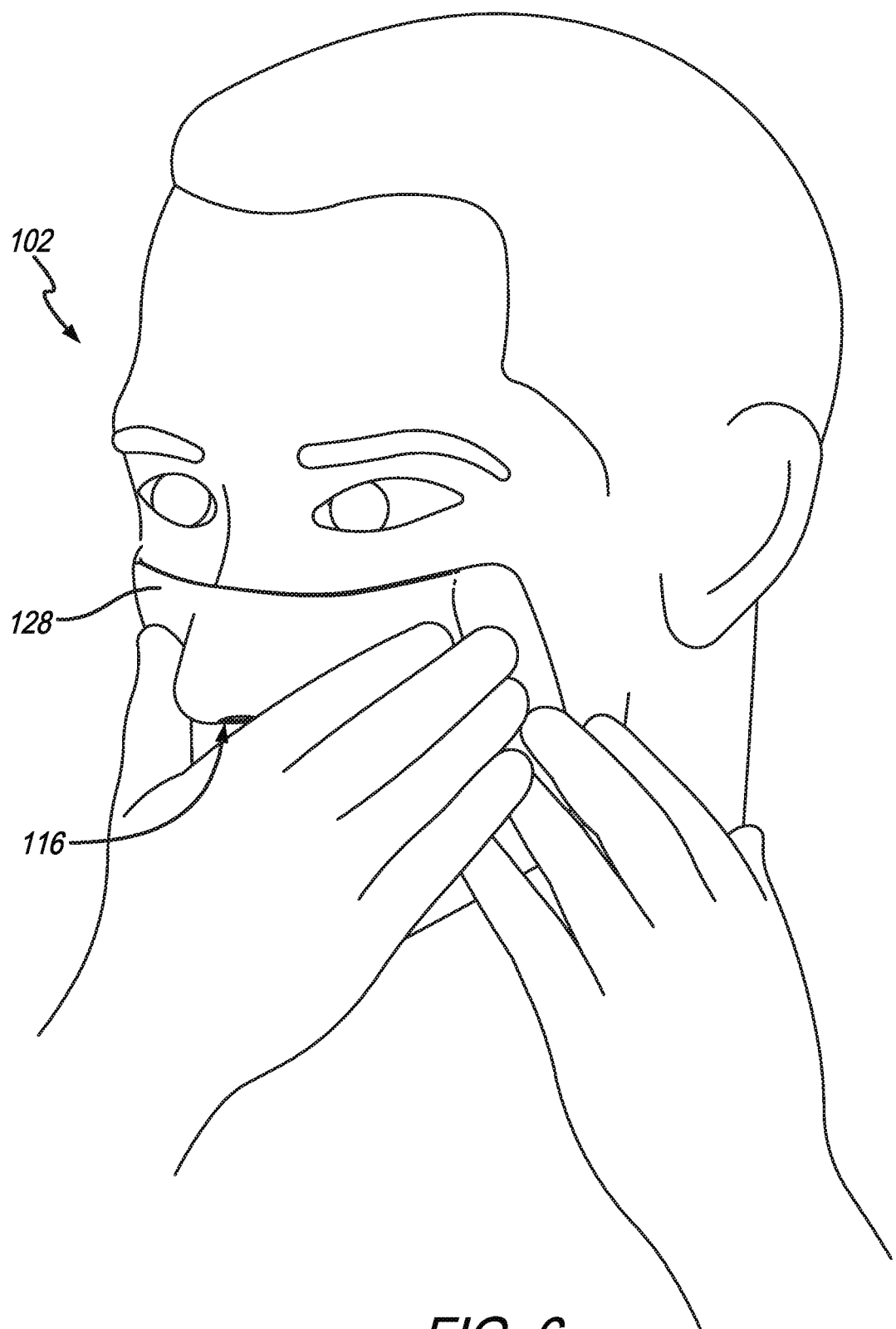
FIG. 6 is a perspective view of a user applying the melted plastic of FIG. 5 to their face in order to create the molded face mask of FIG. 1.

Referring now to FIGS. 5 and 6, the mask 100 can be made in the following manner. A user can purchase polycaprolactone (PCL), which can come in the form of a single 8.5 inch by 11 inch sheet 128 of PCL, approximately ¼ inch thick. The user heats the sheet 128 to the appropriate temperature using water heated on a stove 130, as shown in FIG. 5. Once the sheet 128 is at the appropriate temperature and sufficiently pliable, the user compresses the sheet 128 to their face 102 to mold the sheet 128 to their face 102, as shown in FIG. 6, creating the mask 100. Typically, the mask 100 is held to the face 102 until it hardens. If a user desires one or more nostril openings 116 or mouth openings 132, those openings can be made at this time, when the sheet 128/mask 100 is still malleable. Also at this time, one or more openings 118, 120 can be made on either side of the mask 100 for securing the straps 122 to the mask 100.

Figure 7:
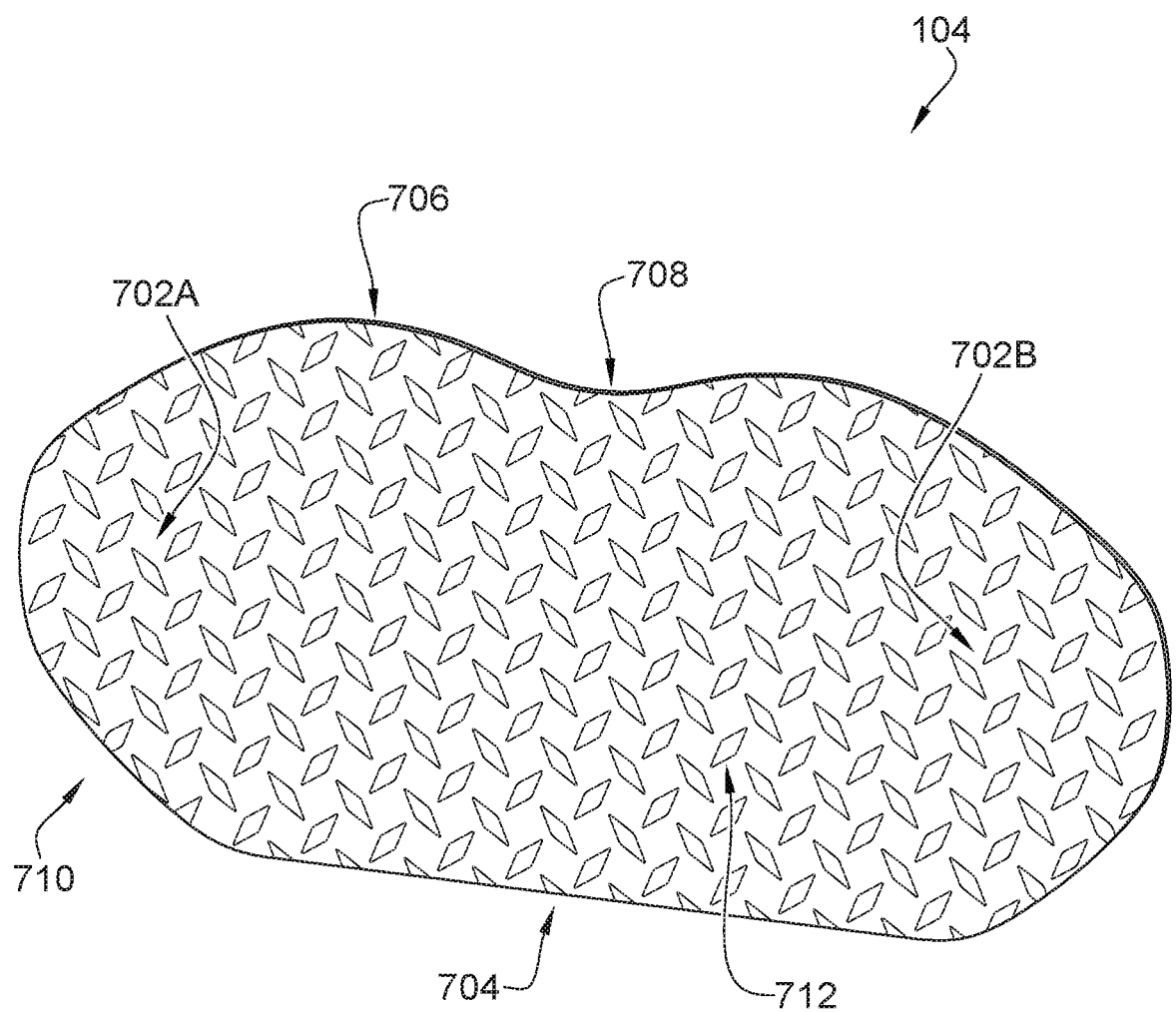
FIG. 7 is a perspective view of a moldable face mask having features of the present invention.

Referring now to FIG. 7, there is shown an embodiment of the mask 100, wherein the body 104 of the mask 100 is pre-formed into the shown shape. The body 104 is roughly oval in shape, comprising two opposed, slightly tapered end portions 702A, 702B, a roughly straight lower edge 704 and an upper edge 706 having a concave section 708 disposed approximately half-way along a length of the upper edge 706. The concave section 708 is designed to fit under a user's nose when the mask 100 is formed to the user's face. In this embodiment, the body 104 has a length of from about 10.5 inches to about 12.5 inches, a height of from about 4.5 inches to about 6.5 inches, and a width of from about ⅛ inch to about 3/16 inch. One exemplary body 104 has a length of about 11.5 inches, a height of about 5.5 inches, and a width of from about ⅛ inch to about 3/16 inch.

The body 104 can comprise an interior surface 710 and an exterior surface 712. The interior surface 710 is disposed proximate a user's face when the mask 100 is being worn, and the exterior surface 712 is disposed distal a user's face when the mask 100 is being worn. Optionally, the body 104 can comprise a pattern disposed on the exterior surface thereof, a shown in FIG. 7. The pattern can comprise diamond plate, coin plate, etc. The pattern is useful for providing a gripping surface, in the event the user wishes to use the face mask 100 without straps, and simply hold it in place on their face.

The mask 100 can either be used with straps 122, or without straps 122. If the mask is used without straps 122, the mask 100 is simply held in place on a users face, with a users hand. When the mask 100 is being molded to the users face, the heated mask 100 is held to the users face for approximately 3 to 5 minutes until the mask 100 cools down, becomes rigid, and retains the facial contours. When using the mask 100 to provide therapeutic relief and reducing redness and bumps associated with facial shaving, the cooled mask 100 is held in place on a user's face for approximately 30 to 45 seconds.

Optionally, as shown in FIG. 7, the present invention can comprise a kit for providing therapeutic relief and reducing redness and bumps associated with facial shaving, the kit comprising: a substantially flat sheet 104 of polycaprolactone plastic, the sheet having: two opposed, slightly tapered end portions 702A, 702B; a generally straight lower edge 704; and an upper edge 706 having a concave portion 708 disposed approximately half-way along a length of the upper edge 706; wherein the sheet 104 can be molded to a user's face to create a rigid face mask.

Although the invention has been described in terms of a preferred embodiment, nevertheless, changes and modifications can be made which do not depart from the spirit, scope and teachings of the invention. Such changes and modifications are deemed to fall within the purview of the present invention as claimed.

What is claimed is:

1. A molded face mask for treating a user's face, the user's face having a nose, the molded face mask comprising:
   a) a rigid, inflexible polycaprolactone body body comprising:
      i) two opposed, slightly tapered end portions;
      ii) a generally straight lower edge; and
      iii) an upper edge having a concave portion disposed approximately half-way along a length of the upper edge for placement below the user's nose; and
   b) coupling means for coupling the molded face mask to the user's face;
   wherein when the face mask is worn by the user, their mouth is covered.

2. The molded face mask of claim 1, wherein the coupling means comprises a first opening disposed proximate a left side edge and a second opening disposed proximate a right side edge.

3. The molded face mask of claim 2, further comprising one or more straps coupled to the first and second opening for securing the molded face mask to the user's face.

4. A method of using a molded face mask, the method comprising the steps of:
   a) providing the molded face mask of claim 1;
   b) cooling the face mask; and
   c) placing the cooled face mask on a user's face after the user shaved their face.

5. The method of claim 4, wherein in step b) the face mask is placed in a refrigerator for cooling.

6. The molded face mask of claim 1, wherein the face mask can be cooled or heated prior to applying to the user's face.

7. The molded face mask of claim 1, wherein when the mask is worn by a user, the concave portion of the upper edge is disposed below the user's nose.

8. The molded face mask of claim 1, wherein the face mask is placed in a refrigerator for cooling prior to applying to the user's face.

9. The method of claim 4, wherein in step b) the face mask cools to room temperature.

10. A kit for providing therapeutic relief and reducing redness and bumps associated with shaving, the kit comprising:
    a) a substantially flat sheet of polycaprolactone plastic, the sheet having:
       i) two opposed, slightly tapered end portions;
       ii) a generally straight lower edge; and
       iii) an upper edge having a concave portion disposed approximately half-way along a length of the upper edge;
       wherein the sheet is configured to be molded to a user's face to create a rigid face mask for placement below the user's nose;
       wherein when the face mask is worn by the user, their mouth is covered.

11. The kit of claim 10, wherein the sheet has a length of from about 10.5 inches to about 12.5 inches, a height of from about 4.5 inches to about 6.5 inches, and a width of from about 1/8 inch to about 3/16 inch.

12. The kit of claim 10, further comprising one or more straps for coupling the mask to the user's face.

13. The kit of claim 10, wherein an outer surface of the sheet comprises a pattern disposed thereon.

14. A method of making a molded face mask, the method comprising the steps of:
    a) providing a substantially flat sheet of polycaprolactone plastic, the sheet having:
       i) two opposed, slightly tapered end portions;
       ii) a generally straight lower edge; and
       iii) an upper edge having a concave portion disposed approximately half-way along a length of the upper;
       wherein the sheet is configured to be molded to a user's face to create a rigid face mask for placement below the user's nose and wherein when the face mask is worn by the user, their mouth is covered;
    b) placing the body in a heating container;
    c) heating the body until it becomes pliable;
    d) placing and pressing the pliable body on a face of a user in order to mold to the face of the user; and
    e) allowing the pliable body to cool, thereby forming the molded face mask.

15. The method of claim 14, further comprising the step of creating a first opening disposed proximate a left side edge and a second opening disposed proximate a right side edge of the molded mask.

16. The method of claim 15, further comprising the step of coupling one or more straps to the first and second openings for securing the molded face mask to the user's face.

* * * * *